US012805988B2

(12) United States Patent
Lim et al.

(10) Patent No.: US 12,805,988 B2
(45) Date of Patent: Nov. 24, 2026

(54) DENTAL BULK BLOCK FOR CUTTING MACHINING AND MANUFACTURING METHOD THEREFOR

(71) Applicant: HASS CO., LTD., Gangwon-do (KR)

(72) Inventors: Hyung Bong Lim, Gyeonggi-do (KR); Yong Su Kim, Gangwon-do (KR)

(73) Assignee: HYOSUNG HEAVY INDUSTRIES CORPORATION, Seoul (KR)

( * ) Notice: Subject to any disclaimer, the term of this patent is extended or adjusted under 35 U.S.C. 154(b) by 518 days.

(21) Appl. No.: 18/473,569

(22) Filed: Sep. 25, 2023

(65) Prior Publication Data

US 2024/0108444 A1 Apr. 4, 2024

Related U.S. Application Data

(63) Continuation of application No. PCT/KR2021/006674, filed on May 28, 2021.

(51) Int. Cl.
*A61C 13/00* (2006.01)
*A61K 6/833* (2020.01)
(Continued)

(52) U.S. Cl.
CPC .......... *A61C 13/0022* (2013.01); *A61K 6/833* (2020.01); *C03B 25/02* (2013.01);
(Continued)

(58) Field of Classification Search
CPC ..... C03C 10/00; C03C 10/0027; C03C 17/04; C03C 2204/04; C03C 3/097;
(Continued)

(56) References Cited

U.S. PATENT DOCUMENTS

| | | | |
|---|---|---|---|
| 2017/0057865 A1 | 3/2017 | Kim et al. |
| 2017/0267575 A1 | 9/2017 | Borczuch-Laczka et al. |
| 2020/0377403 A1 | 12/2020 | Lim et al. |

FOREIGN PATENT DOCUMENTS

| | | |
|---|---|---|
| EP | 3744696 A1 | 12/2020 |
| EP | 3974397 A1 | 3/2022 |

(Continued)

OTHER PUBLICATIONS

Marcus P. Borom et al. "Strength and Microstructure in Lithium Disilicate Glass-Ceramics" Journal of the American Ceramic Society, vol. 58, No. 9-10, Sep. 1, 1975, pp. 385-391.

(Continued)

*Primary Examiner* — Shuangyi Abu Ali
(74) *Attorney, Agent, or Firm* — NKL LAW; Jae Youn Kim

(57) ABSTRACT

Dental bulk blocks for cutting machining are provided. The dental bulk block is a glass ceramic block having a structure in which crystalline phases including lithium disilicate as a main crystalline phase and lithium phosphate and at least one of cristobalite and tridymite as additional crystalline phases in an amorphous glass matrix. The dental bulk block is a functionally graded material (FGM) having gradations of size in the main crystalline phase along a depth direction thereof and having no interface at a gradation value change point at which a gradation value of size in the main crystalline phase changes. The dental bulk block is useful for the manufacture of artificial dental prostheses similar to natural teeth. Therefore, the present disclosure provides the effect of reducing the time and process of manufacturing artificial teeth protheses and increasing structural stability in teams of force distribution by functionally grading physical properties.

18 Claims, 10 Drawing Sheets

(51) Int. Cl.

| | |
|---|---|
| ***C03B 25/02*** | (2006.01) |
| ***C03B 32/02*** | (2006.01) |
| ***C03C 4/00*** | (2006.01) |
| ***C03C 4/02*** | (2006.01) |
| ***C03C 10/00*** | (2006.01) |

(52) U.S. Cl.
CPC ............ *C03B 32/02* (2013.01); *C03C 4/0021* (2013.01); *C03C 4/02* (2013.01); *C03C 10/00* (2013.01); *A61C 2201/002* (2013.01); *C03C 2204/04* (2013.01)

(58) Field of Classification Search
CPC ..... C03C 4/0021; C03C 4/02; A61C 13/0022; A61C 13/083; A61C 2201/002; A61K 6/16; A61K 6/833; C03B 19/02; C03B 25/02; C03B 32/02
See application file for complete search history.

(56) References Cited

FOREIGN PATENT DOCUMENTS

| | | | |
|---|---|---|---|
| JP | 2017-521341 | A | 8/2017 |
| JP | 2018-145084 | A | 9/2018 |
| JP | 2020-193191 | A | 12/2020 |
| KR | 2015-0137573 | A | 12/2015 |
| KR | 2017-0026697 | A | 3/2017 |
| KR | 2018-0018929 | A | 2/2018 |
| KR | 20180102711 | A | 9/2018 |
| KR | 2018-0134002 | A | 12/2018 |
| KR | 10-1975548 | B1 | 4/2019 |
| KR | 2020-0137198 | A | 12/2020 |
| KR | 10-2246195 | A | 4/2021 |

OTHER PUBLICATIONS

International Search Report for corresponding International Application No. PCT/KR2021/006674 mailed Feb. 25, 2022.
Written Opinion for corresponding International Application No. PCT/KR2021/006674 dated Feb. 25, 2022.
Jung et al., "Modulation of Lithium Disilicate Translucency through Heat Treatment", Materials 2021, 14, 2094; https://doi.org/10.3390/ma14092094 published Apr. 21, 2021.

DENTAL BULK BLOCK FOR CUTTING MACHINING AND MANUFACTURING METHOD THEREFOR

CROSS REFERENCE TO RELATED APPLICATION

The present application claims priority to PCT Patent Application No. PCT/KR2021/006674, filed on May 28, 2021, the entire contents of which is incorporated herein for all purposes by this reference.

TECHNICAL FIELD

The present disclosure relates to dental bulk blocks for cutting machining, which are useful for the manufacture of artificial teeth with similar structural characteristics to natural teeth, and a method for manufacturing the same. The present disclosure results from the research carried out with the support of the Gangwon Technopark's project for boosting material/part/equipment companies and supporting independent technology development thereof.

BACKGROUND

Crown materials refer to prosthetic materials for restoring dental parts such as dentin and enamel of a damaged tooth, and may be classified into inlays, onlays, veneers, crowns, and the like, depending on the application area thereof. Since the position where the crown material is placed for restoration is the outer surface of a tooth, highly aesthetic properties are required, and high strength is required due to potential fracture attributable to abrasion with an opposing tooth or chipping. Materials conventionally used as crown materials include leucite glass-ceramics, reinforced porcelain, or fluorapatite crystallized ($Ca_5(PO_4)_3F$) glass. The conventional materials have excellent aesthetic properties but have strength as low as 80 to 120 MPa, thereby being highly prone to fracture. Therefore, research to develop high-strength crown materials is currently underway.

Lithium silicate glass was reported by Marcus P. Borom and Anna M. Turkalo in 1973 (The Pacific Coast Regional Meeting, The American Ceramic Society, San Francisco, CA, Oct. 31, 1973 (Glass division, No.3-G-73P)).

The crystalline phase and strength of $Li_2O$—$Al_2O_3$—$SiO_2$—$Li_2O$—$K_2O$—$B_2O_3$—$P_2O_5$-based glass according to various nucleation conditions and heat treatment conditions for crystal growth have been studied. Crystalline phases in a range of from high-temperature lithium disilicate to low-temperature lithium metasilicate exhibited a strength of 30 to 35 KPS due to the differences in thermal expansion coefficient among base glass, mother glass, $Li_2SiO_5$ phase, and $Li_2SiO_3$ phase.

Materials and methods for manufacturing artificial teeth using glass containing lithium disilicate crystals (monolithic dental crowns) are already disclosed in several patent documents. However, the known arts have difficulty in on-site machining due to the coarse size of the crystalline phase thereof. In addition, for machining, a lithium metasilicate crystalline phase (machinable crystalline phase) needs to be formed in a primary step and heat treatment is performed in a secondary step to obtain a high-strength lithium disilicate crystalline phase. In this case, the accuracy of dimensions is reduced due to shrinkage during the heat treatment, and there is a hassle that the heat treatment needs to be performed. In general, CAD/CAM prosthesis machining requires that a prosthesis be fabricated by directly machining a bulk body in a hospital, and the machined product needs to be applied to the patient as a trial prothesis as quickly as possible (one-day appointment). Therefore, a timely process attributable to heat treatment imposes economical burden on patients and dentists.

In addition, existing lithium disilicate glass has limitations in achieving high optical transmittance or opalescence similar to natural teeth due to their coarse crystalline phase.

In particular, in the case of the existing lithium disilicate crystalline glass, lithium metasilicate glass with good machinability needs to be foamed first for easy machining and then machined, and a secondary crystallization heat treatment process is performed on the lithium metasilicate crystalline glass to form lithium disilicate with improved strength. The lithium disilicate crystalline phase has a size of about 3 μm or more. Therefore, the lithium disilicate has improved strength but has poor machinability.

In order to solve this problem, the applicant of the present disclosure proposed a method for manufacturing crystalline glass containing a lithium disilicate crystalline phase and a silicate crystalline phase with excellent machinability by adjusting the crystal size by changing the primary heat treatment temperature, and the method was granted for a patent under Korean Patent No. 10-1975548. Specifically, the patent document discloses a method for manufacturing crystalline glass for teeth, the method including the steps of: performing a primary heat treatment on a glass composition including 60% to 83% by weight of $SiO_2$, 10% to 15% by weight of $LiO_2$, 2% to 6% by weight of $P_2O_5$ serving as a nucleating agent, 1% to 5% by weight of $Al_2O_3$ for increasing the glass transition point and softening point and improving the chemical durability of glass, 0.1% to 3% by weight of SrO for increasing the softening point of glass, 0.1% to 2% by weight of ZnO, 1% to 5% by weight of a colorant, and 2.5% to 6% by weight of $Na_2O+K_2O$ as alkali metal oxides that increase the thermal expansion coefficient of glass; and performing a secondary heat treatment at 780° C. to 880° C. after the primary heat treatment. By the primary heat treatment, a lithium disilicate crystalline phase and a silica crystalline phase that have a crystal size of 5 nm to 2000 nm are formed, and by the secondary heat treatment, the transmittance of the crystalline phases is adjusted.

On the other hand, with the improvement of human living standards, the demand for aesthetics is increasing in the field of dentistry, and with the increasing aesthetic desire of patients, many studies on aesthetic prosthetic restorations using various materials are being conducted.

In regard to aesthetic restorations that are currently mainly used, the factors that affect the aesthetics of ceramic restorations include the external shape, surface condition, transparency, color tone, etc. of teeth. Among these, transparency is an important factor for successful restorations. Although there have been many studies and developments on the mechanical and physical properties of ceramic restorations for aesthetic prosthetics, there are still many problems with the harmony of color tones, and there are many challenges clinically and technically when it comes to color selection and especially transparency of restorations.

In aesthetic prosthetics, factors that affect the aesthetics of dental restorations include color, shape, and size of teeth, arrangement and ratio of teeth, light rays, permeability, and design of restorations, but the factors that our eyes are actually sensitive to are color and shape.

No part of a natural tooth from the neck to the incisal part displays the sample color.

Considering this point, recently, a method of manufacturing artificial teeth imitating the deep color gradation of natural teeth using a so-called build-up method is also known.

The build-up method refers to a method in which porcelain or zirconia powder is accumulated layer by layer to form colored artificial teeth, and then the colored artificial teeth are heat-treated to mimic naturally layered colors of teeth. Although the method can closely mimic the colors of natural teeth, since the aesthetics of the artificial teeth is entirely dependent on the skill of the technician, the method has poor reproducibility. In addition, since the method does not allow on-site manufacturing, teeth cannot be manufactured on site, the method is not beneficial to the patient, and the is not suitable for cutting machining such as CAD/CAM.

On the other hand, when artificial teeth are manufactured by performing cutting machining such as CAD/CAM on existing bulk blocks, since the bulk blocks are made of a material exhibiting uniform physical properties, the resulting artificial teeth exhibit a single shade of color unlike natural teeth. In particular, when artificial teeth manufactured by the method are applied to front teeth, there is a problem in that the artificial teeth give an aesthetically heterogeneous feeling and thus appear far from natural.

Although the crystalline glass manufacturing method described in Korean Patent No. 10-1975548 owned by the present applicant discloses that transparency and machinability can be adjusted through a secondary heat treatment process, the crystalline glass thus obtained is a block having uniform physical properties through the entire area thereof. Therefore, it is necessary to use a method of combining multiple products to implement deep color gradations like in natural teeth. In other words, it was not easy to implement natural-colored teeth on site by performing cutting machining such as CAD/CAM on a bulk block itself.

By improving the existing bulk block in terms of the point described above, the present applicant filed a patent application and owned a patent (Korean Patent No. 10-2246195) for a bulk block that is useful for manufacturing artificial tooth prostheses similar to natural teeth, with which the time and process of manufacturing artificial tooth prostheses can be shortened, and which is capable of increasing structural stability of artificial teeth by force distribution by giving functional gradients of mechanical properties.

The present disclosure has been devised to provide a gradation bulk block having improved aesthetic properties such as transmittance and shade, being more similar to natural teeth in terms of physical properties, and having improved machinability.

BRIEF SUMMARY

The present disclosure is to provide a dental bulk block for cutting machining, which can be used for the manufacture of artificial tooth restorations that express multi-gradation permeability or physical properties similar to natural teeth, with good reproducibility through cutting machining such as CAD/CAM without using other additional processes.

The present disclosure is to provide a dental bulk block for cutting machining, which has functionally graded physical properties, thereby being capable of shortening the time and process of manufacturing an artificial tooth prosthesis and having the structural stability in terms of force distribution.

The present disclosure is to provide a method for manufacturing a dental bulk block for cutting machining, which can be used for the manufacture of artificial tooth restorations that express multi-gradation permeability or physical properties like natural teeth.

The present disclosure is to provide a method for easily manufacturing a dental restoration by machining the dental bulk block using a machining machine.

One embodiment of the present disclosure provides a dental bulk block for cutting machining, the dental bulk block being a glass ceramic block including crystalline phases in an amorphous glass matrix, in which a main crystalline phase is lithium disilicate and additional crystalline phases include lithium phosphate and at least one selected from cristobalite and tridymite. The dental bulk block is a functionally graded material (FGM) having gradations of size in the main crystalline phase along a depth direction of the dental bulk block and having no interface at a grain size gradation value change point at which a gradation value of size in the main crystalline phase changes.

In a preferred embodiment of the present disclosure, the gradations of size in the main crystalline phase may be formed such that an average grain size falls within a range of 0.05 μm to 1.5 μm.

The dental bulk block according to one embodiment of the present disclosure may also have gradations of light transmittance along the depth direction of the dental bulk block.

In a preferred embodiment, the gradations of light transmittance may be within a range of 25% to 40% at a wavelength of 550 nm.

In a preferred embodiment, the gradations of optical transmittance may appear within a range of 0.5 mm or less in the depth direction.

In a preferred embodiment, the gradations of optical transmittance may appear even within a range of 0.31 mm in the depth direction.

The dental bulk block according to one embodiment of the present disclosure may have gradations of L*, a*, and b* values measured through color difference analysis along the depth direction, and a color deviation (ΔE) value changes even within a range of 0.31 mm in the depth direction.

The dental bulk block according to a preferred embodiment may have a crystallinity of 40% to 70%.

The dental bulk block according to one embodiment of the present disclosure may also have gradations of biaxial flexural strength along the depth direction.

In a preferred embodiment, the gradations of biaxial flexural strength may be within a range of 180 to 420 Mpa.

The dental bulk block according to one embodiment of the present disclosure may be made of a continuous glass matrix.

In a preferred embodiment, the glass matrix may include 65.0% to 73.0% by weight of $SiO_2$, 12.0% to 14.0% by weight of $Li_2O$, 1.5% to 3.0% by weight of $Al_2O_3$, 0.12% to 0.22% by weight of ZnO, and 2.8% to 3.5% by weight of $K_2O$, 0.3% to 1.0% by weight of $Na_2O$, and 2.0% to 6.0% by weight of $P_2O_5$, and a molar ratio of $Al_2O_3$ ($K_2O$+ZnO) falls within a range of 0.3 to 1.2.

In another embodiment of the present disclosure, there is provided a method of manufacturing a dental bulk block for cutting machining, the method including: producing a predetermined form of block by melting a glass composition including 65.0% to 73.0% by weight of $SiO_2$, 12.0% to 14.0% by weight of $Li_2O$, 1.5% to 3.0% by weight of $Al_2O_3$, 0.12% to 0.22% by weight of ZnO, 2.8% to 3.5% by weight of $K_2O$, 0.3% to 1.0% by weight of $Na_2O$, and 2.0% to 6.0% by weight of $P_2O_5$ and satisfying an $Al_2O_3$ ($K_2O$+ZnO) molar ratio of 0.3 to 1.2, shaping and cooling the molten glass composition into in a mold, and annealing the resulting block at a predetermined speed in a temperature range of from 480° C. to 280° C. for a duration of 20 minutes to 2 hours; and heat treating the block at 760° C. to 880° C. with a temperature gradient along a depth direction of the block.

In the dental bulk block manufacturing method according to a preferred embodiment, the heat treating may be performed under conditions in which an upper portion of the block is heat treated in a temperature range of 840° C. to 880° C. and a lower portion of the block is heat treated in a temperature range of 760° C. to 800° C.

In the dental bulk block manufacturing method according to a preferred embodiment, the heat treating may be performed in a graded-temperature heat treating furnace in an operating temperature range of 900° C. to 1100° C. for a duration of 1 to 40 minutes.

One embodiment of the present disclosure provides a method of manufacturing a dental restoration, the method including: manufacturing a predetermined form of dental restoration by machining the dental bulk block according to one of the embodiments using a machining machine; and polishing or glazing the predetermined form of dental restoration.

In the dental restoration manufacturing method according to a preferred embodiment, the glazing may be performed in a temperature range of 730° C. to 820° C. for a duration of 30 seconds to 10 minutes.

The glazing performed under the conditions may correspond to by a general glazing process that is performed in a range that does not impair the inherent optical transmittance of the dental restoration obtained through the previous step.

The glazing may be used to partially adjusting the optical transmittance of the dental restoration obtained through the previous step as needed. In this aspect, the glazing may be performed by heat treatment at 825° C., and the glazing may be used to adjust the optical transmittance of the machined dental restoration. In this case, preferably, the glazing may be performed at a temperature of at least 825° C. for a duration of 1 minute to 20 minutes. In particular, since the optical transmittance is reduced at temperatures at or above 840° C., the glazing temperature may be further increased so that the block may be further partially crystalized when it is needed to lower the optical transmittance.

The bulk block of the present disclosure can be easily used to manufacture an artificial tooth restoration having multi-gradation optical transmittance or physical properties like natural teeth. With the use of the bulk block, the user can easily obtain a dental restoration with controlled transmittance using a simple heat treatment process. Therefore, the present disclosure has an advantage of contributing to simplifying logistics management.

The dental bulk block according to the present disclosure is used to manufacture artificial dental restorations having multi-gradation optical transmittance or physical properties like natural teeth with high reproducibility through only cutting machining such as CAD/CAM without using additional processes. The dental bulk block can shorten the time and process of manufacturing artificial tooth prostheses, and can increase the structural stability in terms of force distribution by functionally grading the physical properties. Such a dental bulk block can be manufactured by applying a simple graded-temperature heat treatment process to a predetermined single glass composition.

Figure 3:
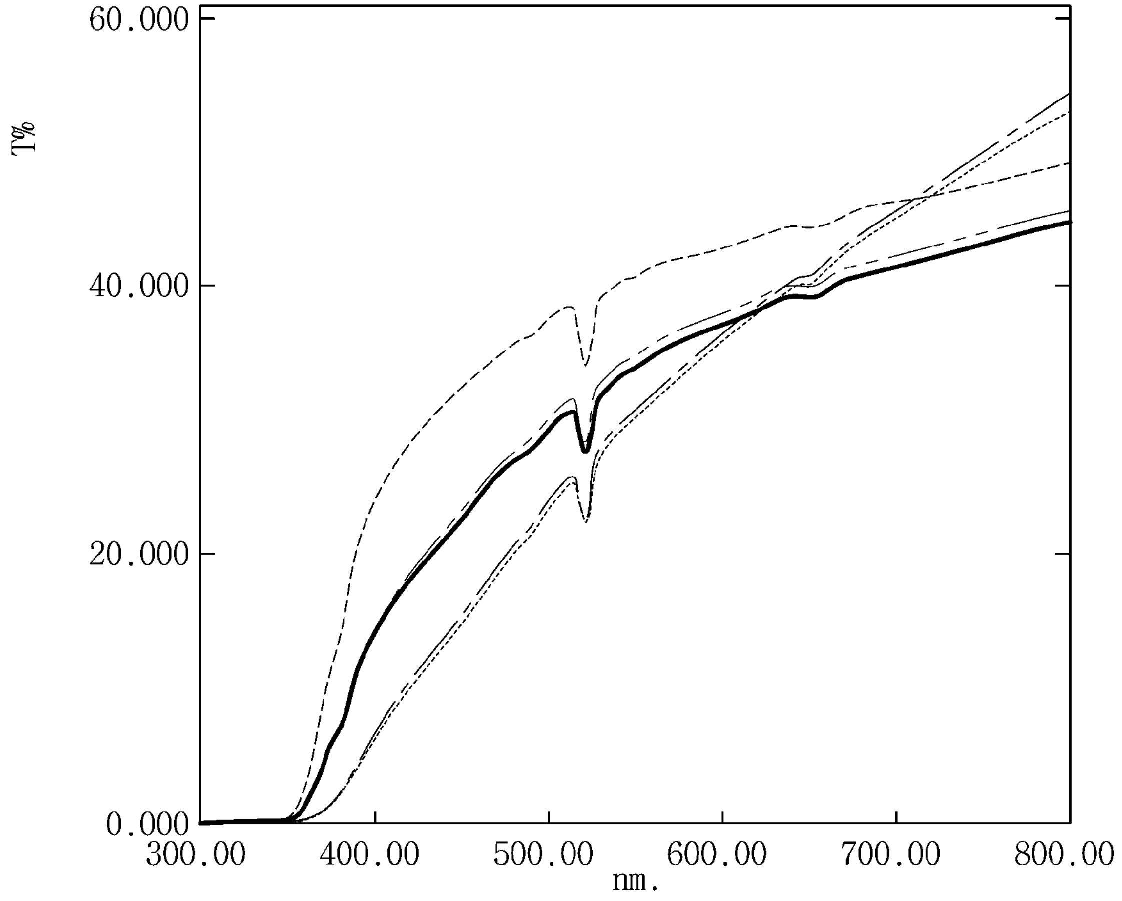
Figure 4:
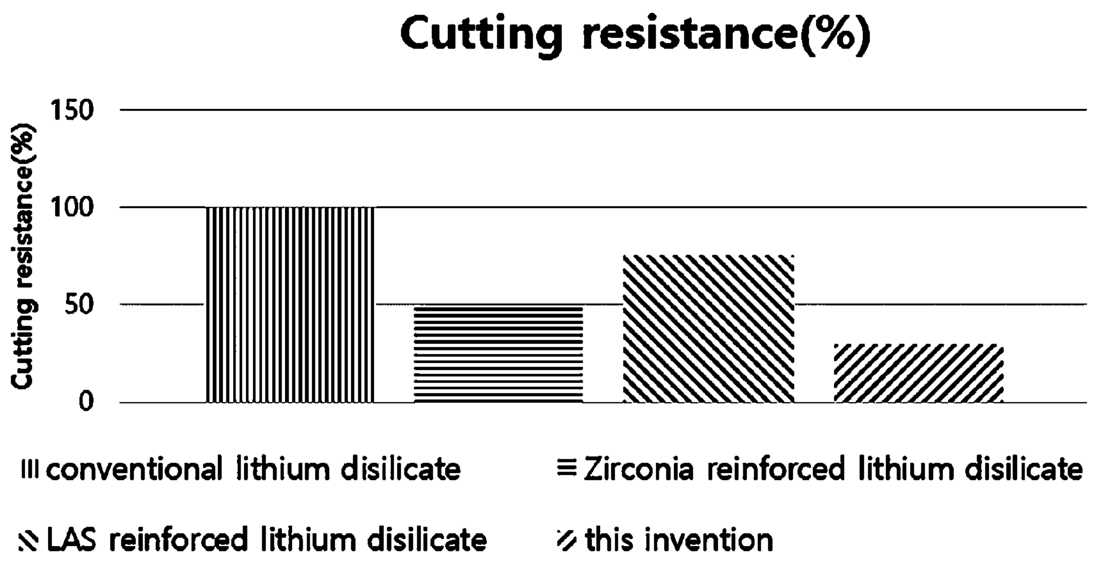
Figure 5:
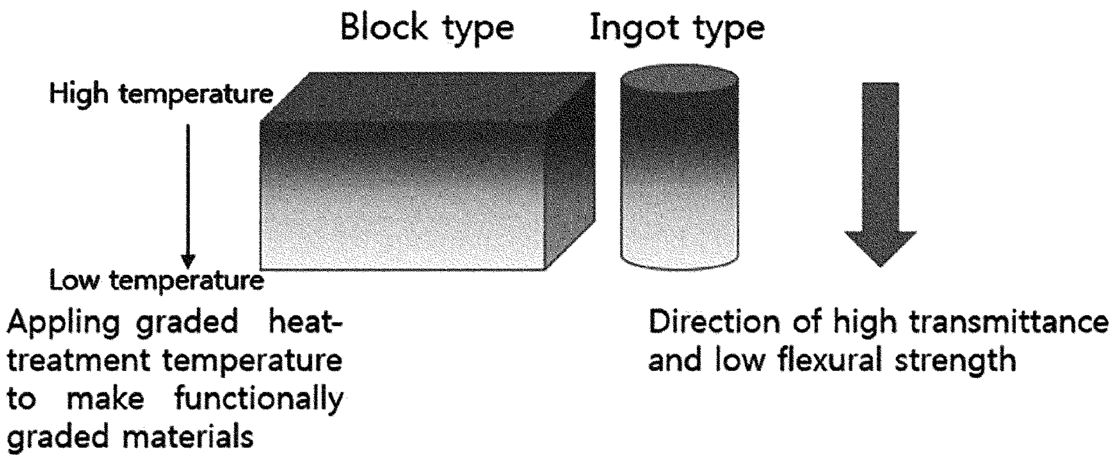
Figure 6:
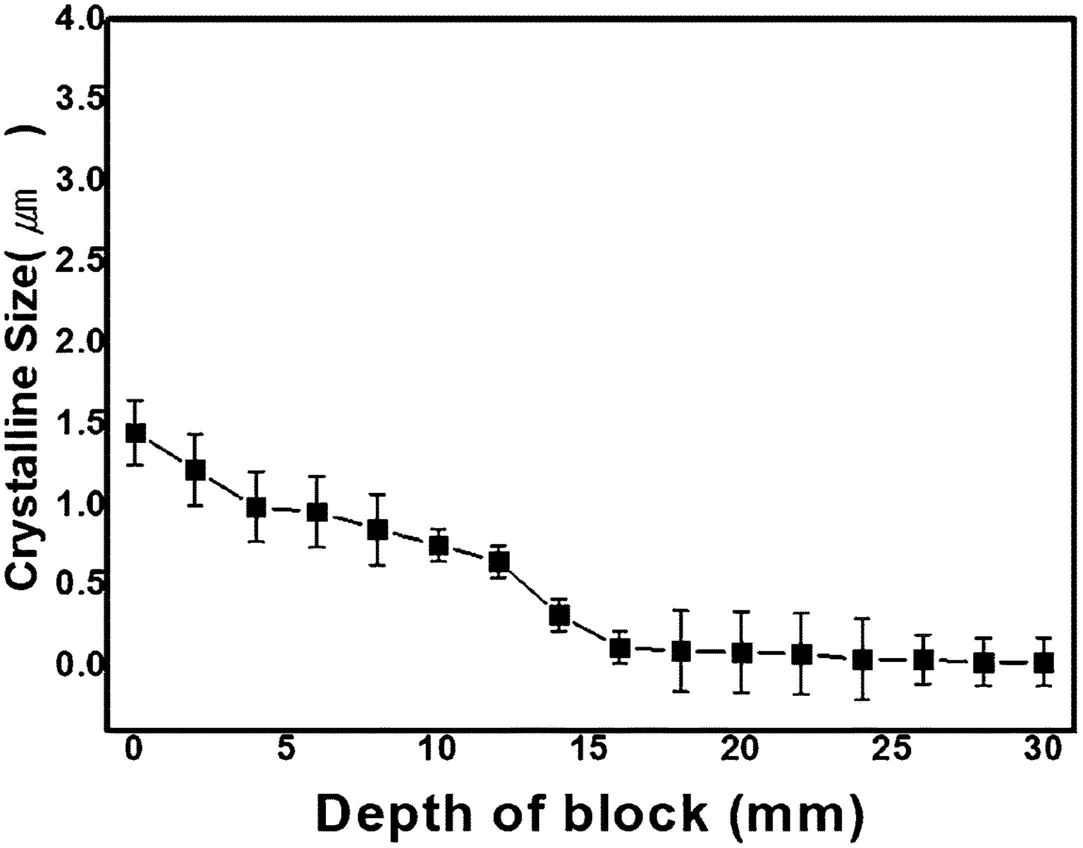
Figure 7:
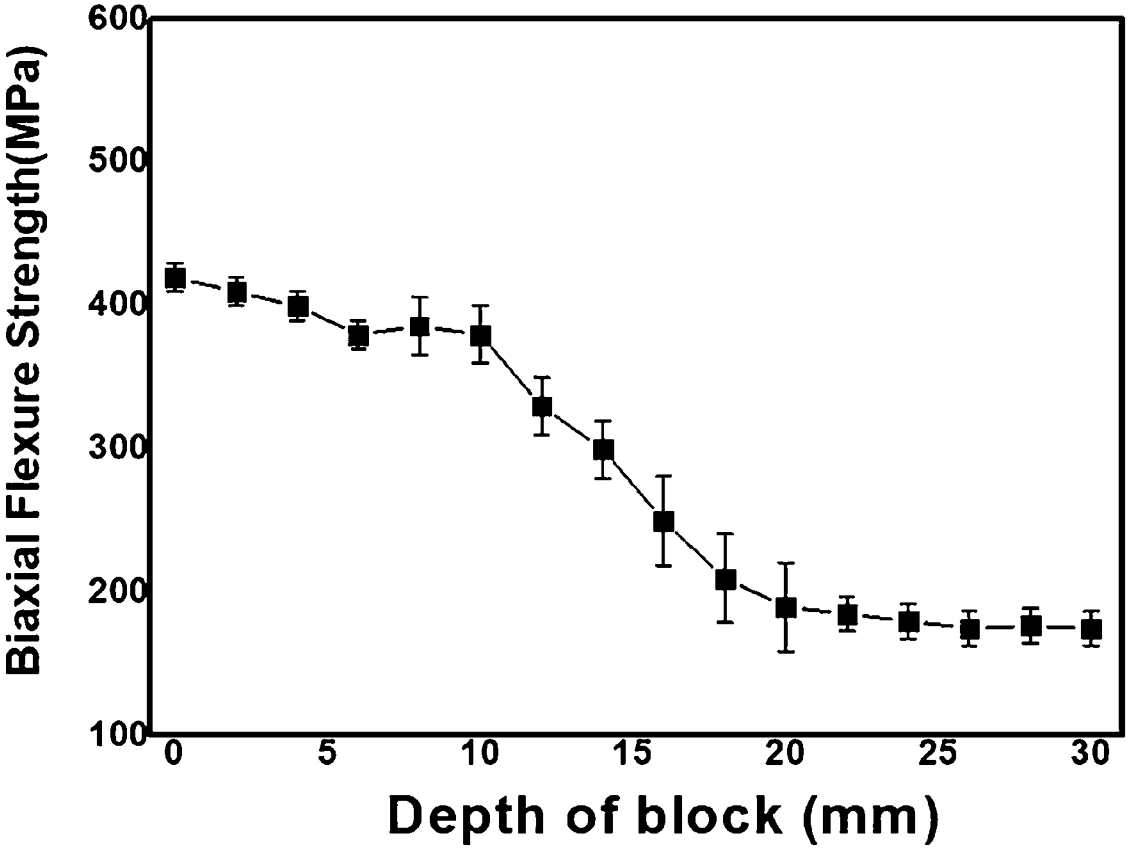

2B is a scanning electron microscope (SEM) image showing changes in the microstructure and crystalline phase size along a depth direction of the bulk block of the present disclosure;

2C is a scanning electron microscope (SEM) image showing changes in the microstructure and crystalline phase size along a depth direction of the bulk block of the present disclosure;

FIG. 3 is a graph of measurements of visible light transmittance for 0.31 mm-thick slice specimens of the bulk block of the present disclosure;

FIG. 4 is a comparative graph of cutting resistance for the bulk block of the present disclosure;

FIG. 5 is a schematic diagram showing one exemplary method for manufacturing a dental bulk block of the present disclosure;

FIG. 6 is a graph showing grain sizes of the main crystalline phase according to the depths of a bulk block obtained according to an embodiment of the present disclosure; and FIG. 7 is a graph showing variation in biaxial flexural strength according to the depths of a bulk block according to an embodiment of the present disclosure.

Figure 8:
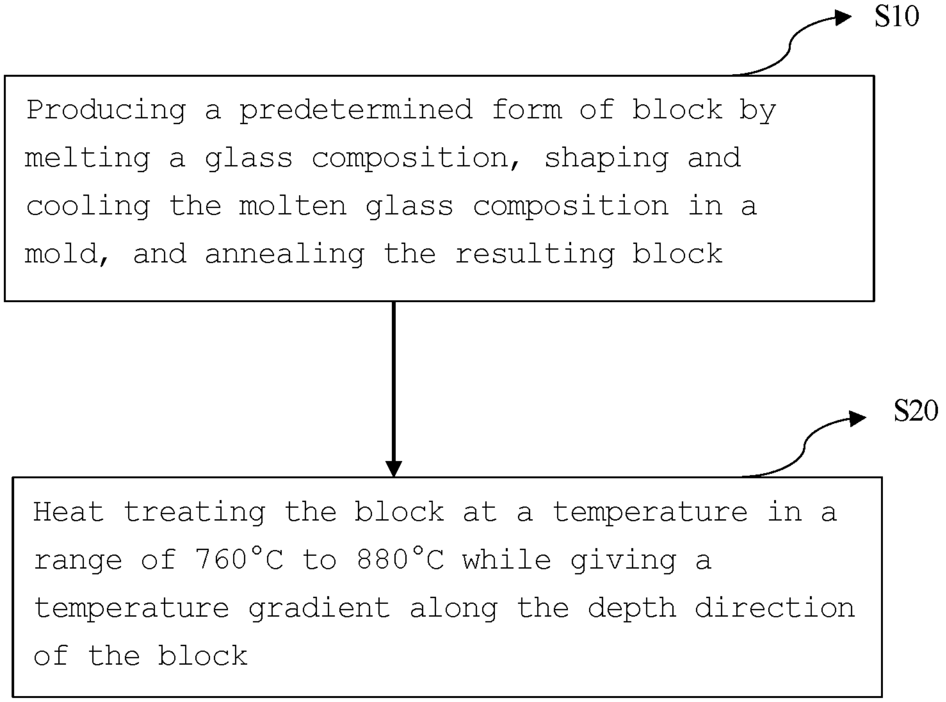

FIG. 8 illustrates an example flowchart for manufacturing a machinable dental bulk block in accordance with an embodiment of this disclosure.

Figure 9:
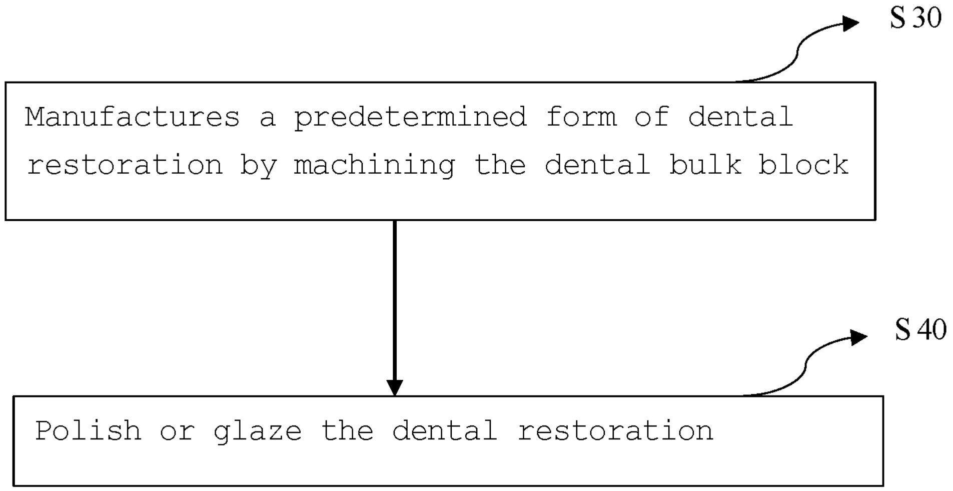

FIG. 9 illustrates an example flowchart for manufacturing a dental restoration in accordance with an embodiment of this disclosure.

DETAILED DESCRIPTION

The foregoing and other aspects of the present disclosure will become more clearly understood through preferred embodiments described with reference to the accompanying drawings. Hereinafter, embodiments of the present disclosure will be described in detail such that those skilled in the art can easily understand and reproduce them.

A dental bulk block for cutting machining, according to the present disclosure, is a glass ceramic block including crystalline phases in an amorphous glass matrix, in which the main crystalline phase is lithium disilicate and additional crystalline phases include at least one selected from cristobalite and tridymite, and lithium phosphate. The dental bulk block is a functionally graded material having gradations of grain size in the main crystalline phase along a depth direction and having no interface at a gradation change point at which a gradiation value of size in the main crystalline phase changes.

In the description above and below, the term "main crystalline phase" is defined as a crystalline phase that accounts for at least 80% by weight with respect to the total weight of all the crystalline phases, and the term "additional crystalline phase" is defined as the remaining crystalline phase other than the main crystalline phase.

The content of each crystalline phase can be calculated through X-ray diffraction analysis. For example, in a specimen composed of two polymorphs "a" and "b", the ratio Fa of the crystalline phase "a" is quantitatively represented by Equation 1 below.

$$F_a = \frac{1}{1 + K\left(\frac{I_b}{I_a}\right)} \quad \text{[Equation 1]}$$

This value can be obtained by measuring the intensity ratio of two crystalline phases and obtaining the constant K. K is the ratio $I_{oa}/I_{ob}$ of absolute intensities of two pure polymorphs and is obtained by measuring standard substances.

In the description above and below, the term "main crystalline phase" may be defined on the basis of the content calculated according to this method.

In addition, when described as "having gradations of grain size in a main crystalline phase along a depth direction", it means that when the grain sizes of the main crystalline phase are plotted as a function of depth of the bulk block in a graphical representation, there is a gradient of changes in grain size of the main crystalline phase. That is, it means that the grain sizes of the main crystalline phase size are represented as gradations along the depth of the bulk block.

Also, the term "grain size gradation value change point of a main crystalline phase size" refers to a point at which the gradation value of the grain size of the main crystalline phase substantially changes when the grain sizes of the main crystalline phase are plotted as a function of a depth of a bulk block. Here, the expression "substantially change" may mean a change as a single value, but may also include a change that is substantial in view of the distribution of the values.

In addition, the expression "no interface exists at a grain size gradation value change point of a main crystalline phase" means that there is no significant interface representing interlayer separation at a certain depth-wise point at which the gradation value of grain size of the main crystalline phase changes. That is, it means that the bulk block has continuous gradations of grain size of the main crystalline phase without an interface in the depth direction.

On the other hand, the term "functionally graded material (FGM)" refers to a material in which the properties of the material continuously change from one surface to the opposite surface. In the present disclosure, although there is practically no separation in variations, the term "functionally graded material" is borrowed in terms that the properties of a material seamlessly change.

In the description above and below, the bulk block is not limited in its shape. For example, bulk bodies of various forms such as a block form, a disk foam, an ingot form, a cylinder form, etc. can be used.

The bulk block according to the present disclosure contains lithium disilicate as the main crystalline phase and lithium phosphate and at least one selected from cristobalite and tridymite as additional crystalline phases. That is, the bulk block does not contain any other crystalline phases except for lithium disilicate, lithium phosphate, and at least one of cristobalite and tridymite.

Figure 1:
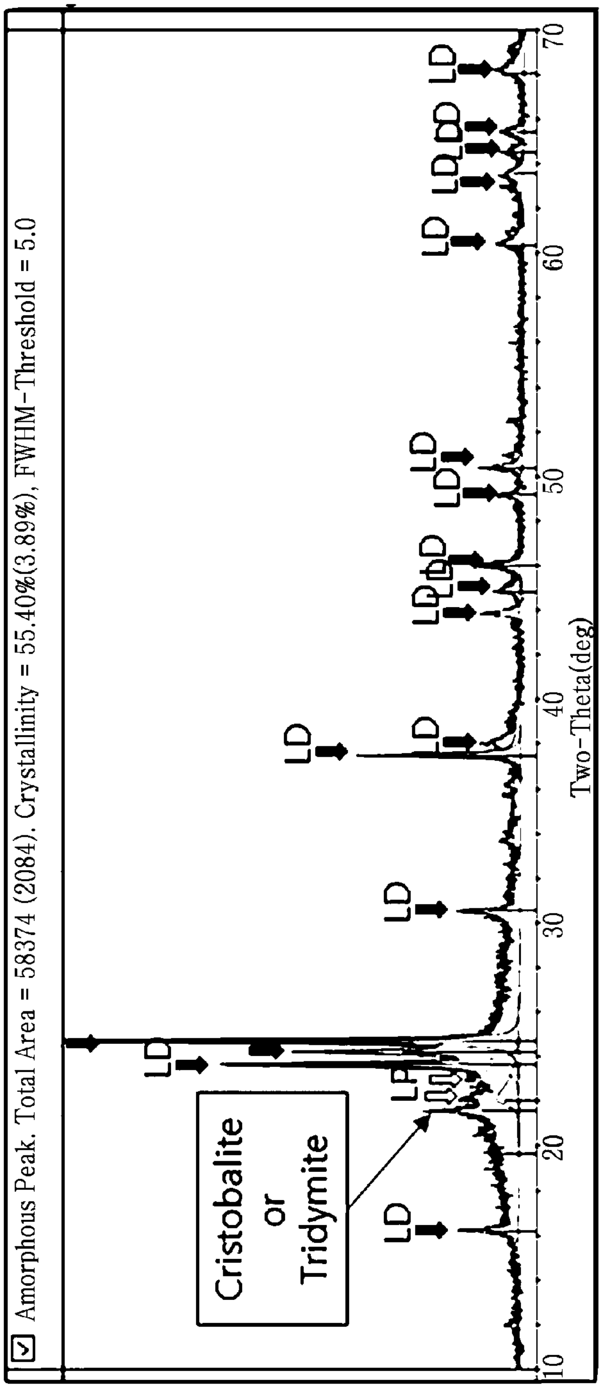
FIG. 1 is a graph of an X-ray diffraction analysis result of a bulk block according to the present disclosure.

A graph of XRD analysis results for the bulk block according to a preferred embodiment is as shown in FIG. 1.

In FIG. 1, the main crystalline phase of the dental bulk block according to one embodiment of the present disclosure is lithium disilicate. Since an additional peak appears at 2 θ=21.7°, an additional crystalline phase is assumed to be a polymorph of $SiO_2$, i.e., cristobalite (JCPDS #39-1425, 2 θ=21.83° main peak) or tridymite (JCPDS *01-0378, 2 θ=21.76°). Since an additional peak appears at 2 θ=22.18° and 22.9°, a further additional crystalline phase may be identified as lithium phosphate (JCPDS #15-0760, main peaks at 2 θ=22.3° and 23.1).

In the description above and below, the XRD analysis will be understood as the result of analysis performed using an X-ray diffraction analyzer (D/MAX-2500, Igaku, Japan; Cu Kα (40 kV, 60 mA), scanning speed of 6°/min, 2 θ:10° to 70°, Rigaku, Japan).

These crystalline phases can be changed into microcrystals having various sizes and size distributions according to temperature, thereby exhibiting diverse mechanical properties and light transmittances.

In addition, since the bulk block has gradations of grain size in the main crystalline phase along a depth direction of the bulk block, the bulk block may exhibit graded light transmittances and graded mechanical properties along the depth direction. Furthermore, since there is no interface at the point where the gradation value of the grain size of the main crystal phase changes, interlayer bonding is not required, and the problem of layer separation during cutting can be solved. In addition, it is possible to provide an artificial tooth prosthesis with increased structural stability in tams of force dissipation due to such graded functionalization.

In the bulk block of the present disclosure, the gradations of grain size of the main crystalline phase may be implemented such that an average grain size falls within a range of 0.05 μm to 1.5 μm.

Figure 2A:
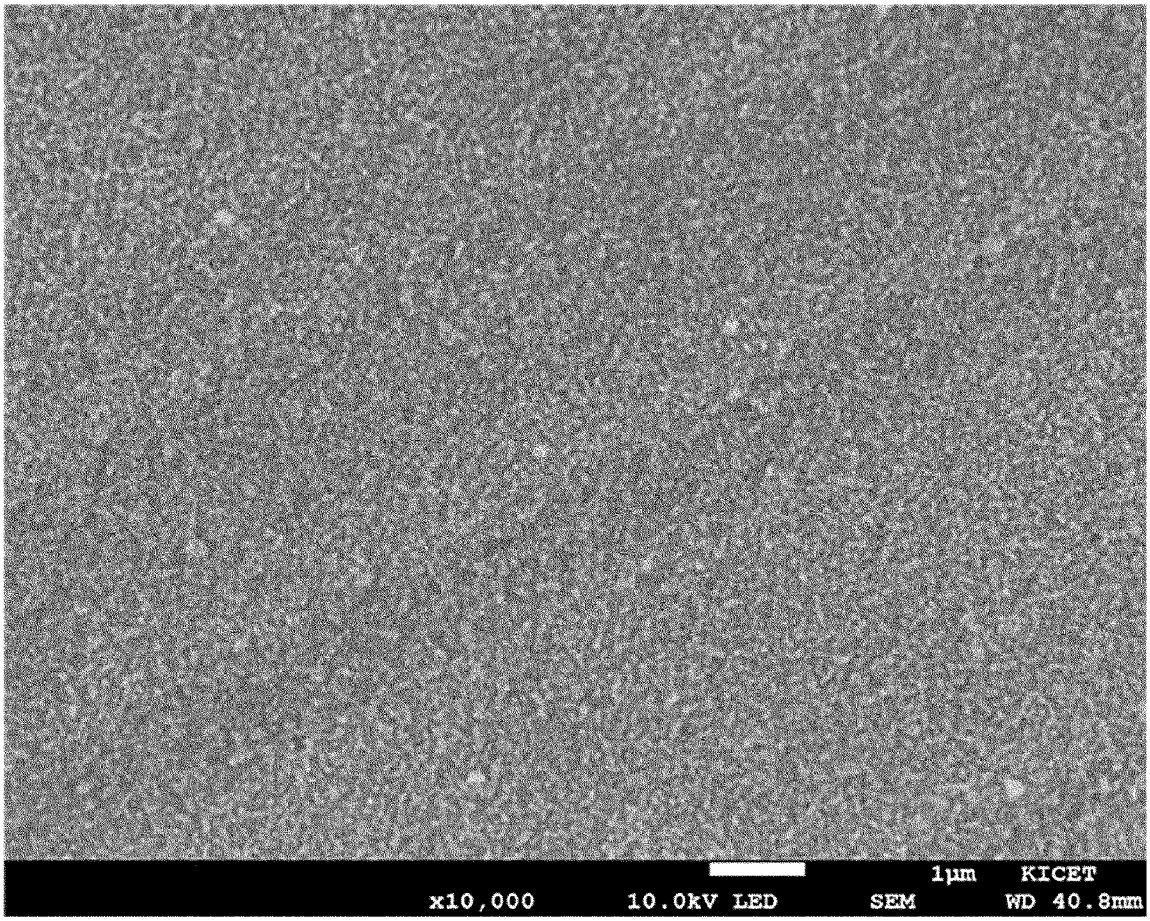
FIG. 2A is a scanning electron microscope (SEM) image showing changes in the microstructure and crystalline phase size along a depth direction of the bulk block of the present disclosure.
Figure 2B:
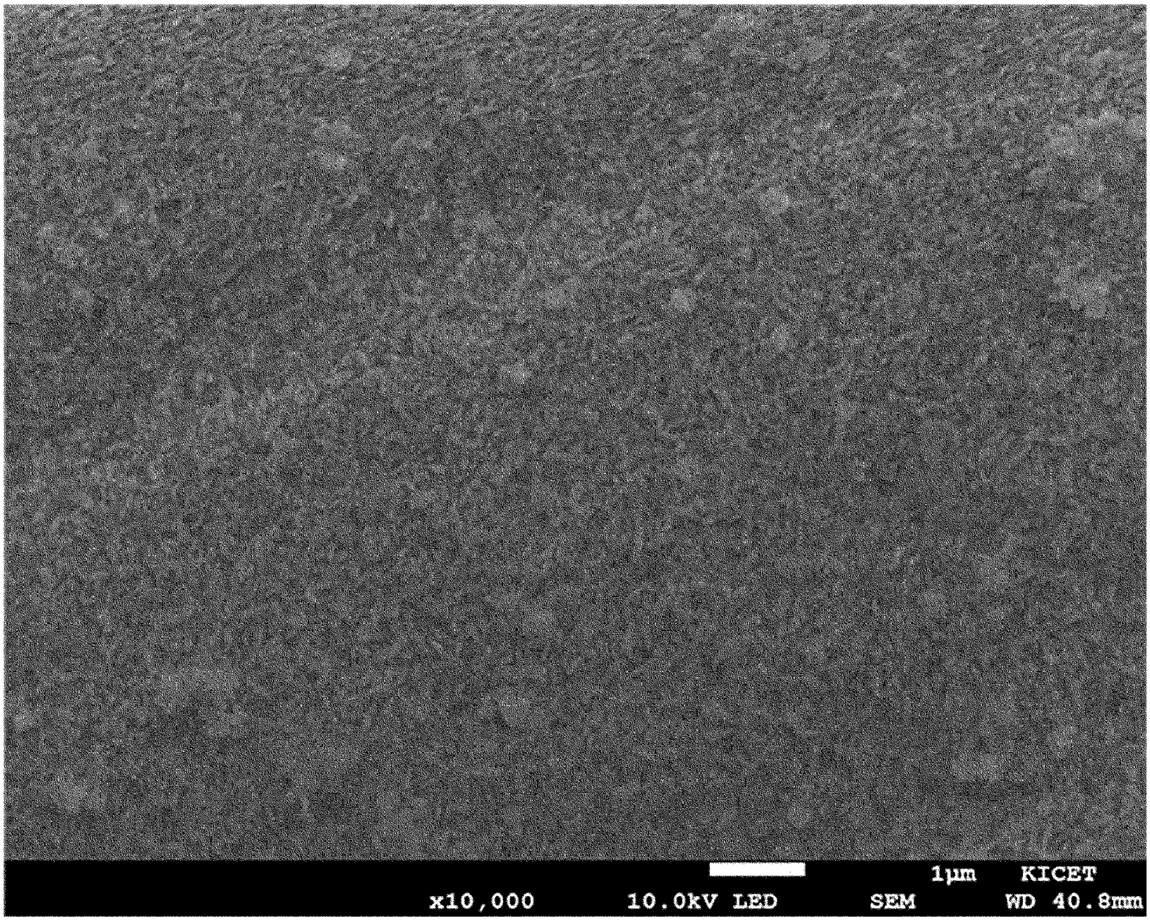
Figure 2C:
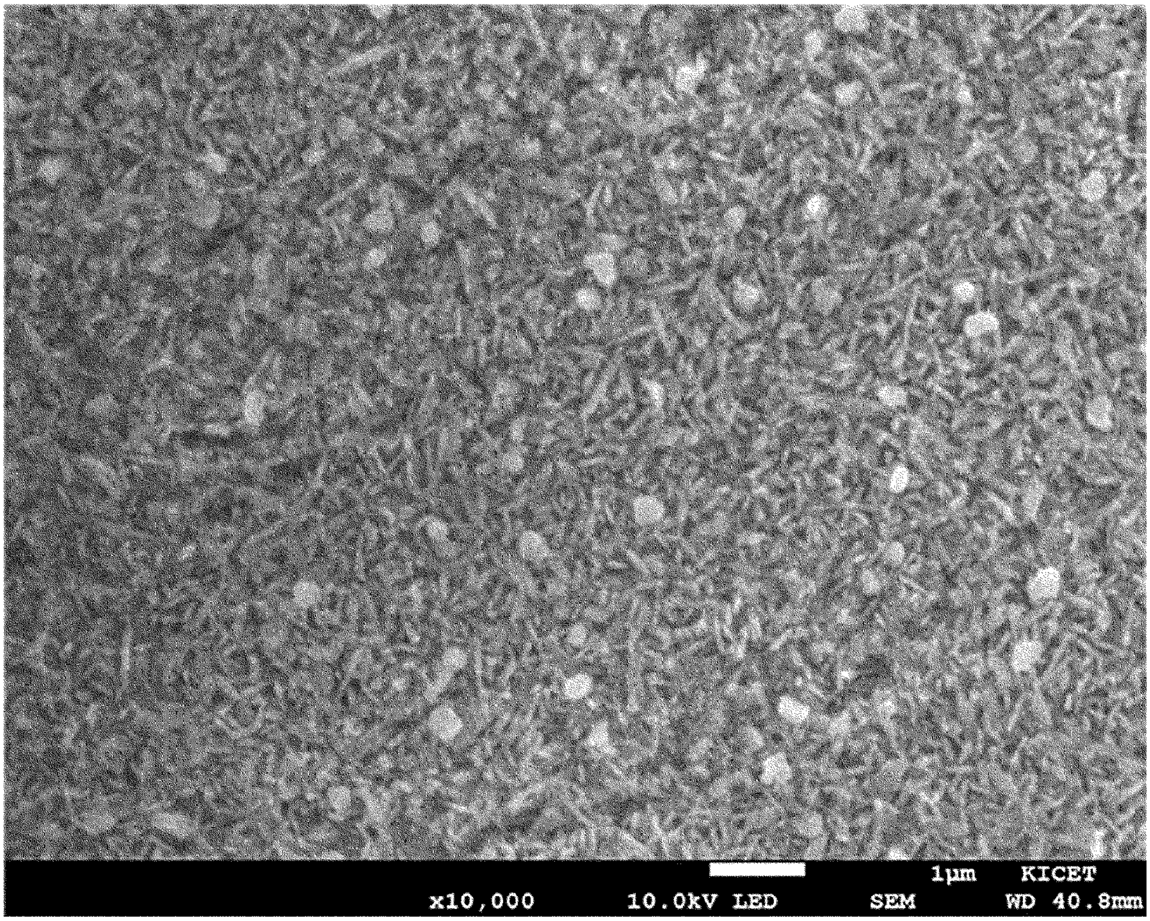

For example, FIG. 2 shows a scanning electron microscope (SEM) image of the dental bulk block of the present disclosure. FIG. 2*a* is a low temperature portion (bottom) of the block subjected to gradient heat treatment, FIG. 2*b* is an intermediate temperature portion, and FIG. 2*c* is a high temperature portion (top layer). Specifically, FIG. 2*a* is an SEM image of a lower layer portion (depth: 20 mm) of the block, FIG. 2*b* is an SEM image of a middle portion (depth: 10 mm), and FIG. 2*c* is an SEM image of an upper layer portion (depth: 0.5 mm).

The average size of the crystalline grains can be derived from the SEM images using the linear intercept method. Specifically, by drawing a diagonal line or a random straight line on each of the SEM images and dividing the number of crystalline phases through which the straight line passes by the length of the straight line, the average size of the crystalline grains can be obtained, taking the magnification into account.

It will be understood that the grain size of the crystalline phase in the description above and below is calculated according to this method.

The bulk block of the present disclosure is a functionally graded material. Since this functionally graded material is subjected to cutting machining such as CAD/CAM under the same processing conditions, the gradations of size of the main crystalline phase may be determined such that the average grain size falls within a range of 0.05 μm to 1.5 μm in terms of machinability and permeability that can be clinically applicable to artificial teeth restorations.

As described above, the dental bulk block of the present disclosure has gradations of optical transmittance along the depth direction thereof because it has gradations of grain size of the main crystalline phase along the depth direction.

In particular, considering the average grain size range in the crystalline size gradation range, the gradations of optical transmittance may be in a range of 25% to 40% at a wavelength of 550.

The optical transmittance in the above and below description is measured using a UV-visible spectrometer (UV-2401PC, Shimadzu, Japan).

As described above, the dental bulk block of the present disclosure does not have an interface at the point where the gradation value of the main crystal phase changes. In this respect, the gradations of optical path appear in a depth-wise range of 0.5 mm or less of the dental block and substantially in a depth-wise range of 0.31 mm or less.

In order to measure the optical transmittance of the dental bulk block according to the present invention for each gradient position, after a sample is sliced to have about 0.31 mm in the depth direction along which the transparency decreases, the surface of the sliced specimen is cleaned using ethanol, and the optical transmittance of the sliced specimen was measured using a UV-visible spectrometer (UV-2401PC, Shimadzu, Japan). In this case, the measurement wavelength range was 300 to 800 nm, and the slit width was 2.0 nm. It can be seen from the results of FIG. 3 that there is a difference in transmittance for the sliced specimens with a thickness of 0.31 mm.

In FIG. 3, each specimen corresponds to a specimen by depth in Table 1 below.

TABLE 1

| Specimen No. | Depth (mm) |
|---|---|
| 1 | 0.31 |
| 2 | 0.62 |
| 3 | 0.93 |
| 4 | 1.24 |
| 5 | 1.55 |

This result can be seen as meaning that the optical transmittance value changes even within the range of 0.31 mm in the depth direction, that is, the gradations of transmittance appear within the thickness. This result clearly shows that that the dental bulk block of the present disclosure is a functionally graded material. In addition, this transmittance measurement result confirms that an artificial tooth having excellent esthetics and appropriate hiding properties can be obtained.

In another aspect, the dental bulk block of the present disclosure also has gradations of shade, and specifically gradations of L*, a* and b* values along the depth direction according to color difference analysis. As described above, the dental bulk block of the present disclosure does not have an interface at the point where the gradation value of the main crystal phase changes. In this respect, the color deviation (ΔE) value changes within a depth of 0.31 mm or less.

Color standardization was necessary for accurate measurement, transmission, and reproduction of color, and thus a color system was devised. Many color systems have been proposed, and among them, the most widely used is the CIE L*a*b* color space defined by the Commission International de l'Eclairage (CIE) in 1976. Here, L* represents lightness, and a* and b* represent chromaticity coordinates. In the coordinates, a larger L* value indicates a brighter color and a smaller L" value indicates a darker color, +a* indicates red, −a* indicates green, +b* indicates yellow, and −b* indicates blue.

In order to measure the color of the dental bulk block according to the present disclosure by gradient position, the dental bulk block is cut at a depth of about 0.31 mm in the depth direction along which the transparency decreases, the surface of the sliced specimen is cleaned using ethanol, and the analysis is performed using a UV-visible spectrometer (UV-2401PC, Shimadzu, Japan). In this case, the measurement wavelength was in a range of 380 to 780 nm, and the slit width was 2.0 nm. After setting a baseline using a reference sample, the reflectance of the specimen was measured to obtain an L*a*b* color system. The measurement was performed three times, and average values were used as the measured L*a*b* values to reduce an error. Using these three values, ΔE representing the color deviation was obtained. A ΔE value of 0 for the two specimens means that there is no difference in color, and a ΔE value between 0 and 2 means that there is a very slight difference in color. A ΔE value of 2 to 4 means that the color difference is noticeable, and a ΔE value of 4 to 6 means that the color difference is appreciable. A ΔE value of 6 to 12 means that the color difference is significant (much), and a ΔE value of 12 or more means that the color difference is considerably significant (very much).

In the case of a dental bulk block that is a glass ceramic block having a structure in which crystalline phases exists in an amorphous glass matrix, in which the main crystalline phase is lithium disilicate and additional crystalline phases include lithium phosphate and at least one selected from cristobalite and tridymite, and the dental bulk block is a functionally graded material (FGM) having gradations of grain size in the main crystalline phase along a depth direction of the dental bulk block and having no interface at a grain size gradation value change point at which a gradation value of grain size in the main crystalline phase changes, as illustrated in FIGS. 1 and 2, the following results in Table 2 show that the color deviation (ΔE) with depth ranges from 3.6 to 5.7 for 0.31 mm-thick sliced specimens. These results show that the color deviation (ΔE) value changes even within a range of 0.31 mm in the depth direction, which means that different gradations of color appear even within this thickness. In another aspect, these results clearly show that the dental bulk block of the present disclosure is a functionally graded material.

TABLE 2

| Specimen No. | Depth (mm) | L * | a* | b* | ΔE |
|---|---|---|---|---|---|
| 1 | 0.31 | 66.70 | −1.50 | 8.70 | |
| 2 | 0.62 | 71.00 | −1.70 | 12.30 | 5.611 |
| 3 | 0.93 | 73.80 | −3.40 | 13.90 | 3.645 |
| 4 | 1.24 | 75.40 | −2.60 | 10.20 | 4.109 |
| 5 | 1.55 | 77.40 | −3.10 | 6.10 | 4.589 |

In addition, the dental bulk block of the present disclosure has gradations of biaxial bending strength depending on the depth. In particular, considering the average grain size range for the gradations of grain size of the crystalline phase, the gradations of biaxial flexural strength may be in a range of 180 to 420 MPa. On the other hand, the dental bulk block of the present disclosure may preferably have a crystallinity of 40% to 70% in terms of processability and implementation of functional gradations of various physical properties as described above.

In the description above and below, "crystallinity" may be defined as the ratio of the crystalline phases to the amorphous glass matrix, and it can be achieved by various methods. In one embodiment of the present disclosure, it is a value that is automatically calculated using an X-ray diffractometer.

The dental bulk block of the present disclosure is a glass ceramic block having a structure in which crystalline phases precipitate in a continuous amorphous glass matrix, in which the main crystal phase is lithium disilicate and the additional crystal phases are lithium phosphate and at least one of cristobalite and tridymite. The dental bulk block is a functionally graded material having gradations of grain size in the main crystalline phase along a depth direction thereof and having no interface at gradation value change point of the grain size of the main crystalline phase.

In the description above and below, the term "continuous glass matrix" may be defined as a glass matrix in which no interlayer interfaces exist and which has a composition that is unform through the entire body thereof.

Preferably, the glass matrix contains 65.0% to 73.0% by weight of $SiO_2$, 12.0% to 14.0% by weight of $Li_2O$, 1.5% to 3.0% by weight of $Al_2O_3$, 0.12% to 0.22% by weight of ZnO, 2.8% to 3.5% by weight of $K_2O$, 0.3% to 1.0% by weight of $Na_2O$, and 2.0% to 6.0% by weight of $P_2O_5$, and the $Al_2O_3$ ($K_2O$+ZnO) molar ratio of the glass matrix may fall within a range of 0.3 to 1.2.

The glass composition is subjected to heat treatment for crystal nucleation and for crystal growth so that crystalline phases precipitate in an amorphous glass matrix. The temperature at which the crystal growth occurs in the glass matrix is in a range of 760° C. and 880° C. That is, the crystal nucleation starts at a temperature of at least 490° C., and the crystal growth occurs as the temperature increases. The grown crystals exhibit the lowest optical transmittance for use as an artificial tooth at a temperature of at most 880° C. That is, the optical transmittance gradually decreases from the temperature at which the crystal starts growing up to a maximum temperature of 880° C. When focusing on the crystal growth, when the crystal growth is implemented in one bulk block, it is possible to imitate multiple color gradations as in natural teeth.

Not only a single tooth itself exhibits locally different optical transmittances, but also every tooth exhibits different optical transmittances. If the variation in optical transmittance according to the heat treatment temperature can be implemented in one bulk block, multiple gradations of natural teeth can be successively realized.

From this point of view, the present disclosure provides a method for manufacturing a dental bulk block for cutting machining, the method including: producing S10 a predetermined form of block by melting a glass composition containing 65.0% to 73.0% by weight of $SiO_2$, 12.0% to 14.0% by weight of $Li_2O$, 1.5% to 3.0% by weight of $Al_2O_3$, 0.12% to 0.22% by weight of ZnO, 2.8% to 3.5% by weight of $K_2O$, 0.3% to 1.0% by weight of $Na_2O$, and 2.0% to 6.0% by weight of $P_2O_5$ and satisfying an $Al_2O_3$ ($K_2O$+ZnO) molar ratio of 0.3 to 1.2, shaping and cooling the molten glass composition in a mold, and annealing the resulting block while changing a temperature from 480° C. to 280° C. at a predetermined rate for a duration of 20 minutes to 2 hours; and heat treating S20 the block at 760° C. to 880° C. with a temperature gradient along a depth direction of the block.

As described above, the glass composition has a characteristic of exhibiting different optical transmittances according to a heat treatment temperature range. Therefore, when the entire block is uniformly heat treated, the entire block exhibits uniform optical transmittance. However, when the block is heat treated with a temperature gradient, the block exhibits locally different optical transmittances or physical properties (i.e., gradations of optical transmittance and physical property).

A bulk block, it is used as a workpiece for machining such as CAD/CAM machining. In the manufacturing manufacturing method of the present disclosure, heat is applied with a temperature gradient in the depth direction of the block when the block is heat-treated. Therefore, a bulk block with multiple gradations of optical transmittance and strength can be obtained.

Conventional types of crystallized glass have coarse crystal sizes, making it difficult to control optical transmittance of the glass and to perform machining on the glass. However, in the case of the glass composition prepared for the present disclosure, microcrystals can be formed. The glass composition has various grain sizes and exhibits locally different grain size distributions, physical properties, and optical transmittances depending on temperatures. Taking advantage of this characteristic, a single bulk block that exhibits multiple gradations of physical properties and optical transmittance can be implemented by a method in which a single block is prepared from a glass composition, and the block is subjected to temperature-graded heat treatment giving a temperature gradient in a depth direction of the block.

Here, when described as "temperature-graded heat treatment giving a temperature gradient in a depth direction of a block", it may refer to a full-range gradual temperature gradient in which the temperature gradually increases from the bottom to the top of the block in the depth direction or to a local temperature gradient in which the block has locally different temperatures. Of course, the selection of the temperature gradients may be made according to the characteristics of the patient's natural teeth requiring an artificial tooth prosthesis or according to the unique characteristics of the part of the tooth requiring the prosthesis.

However, considering typical natural teeth, it may be preferable to use temperature-graded heat treatment giving a full-range gradual temperature gradient in which the temperature gradually increases from the bottom to the top of the block in the depth direction.

In a preferred embodiment, the heat treatment step is performed so that an upper layer of the block is heat-treated in a temperature range of 840° C. to 880° C., and a lower layer of the block is heat-treated in a temperature range of 760° C. to 800° C. To give this temperature gradient, the actual heat treatment is preferably performed in a temperature-graded furnace in an operating temperature range of 900° C. to 1,100° C. for a duration of 1 minute to 40 minutes.

In the case of using the above-described heat treatment method and the glass composition according to the present disclosure, it is possible to imitate the structure of a natural tooth in which the optical transmittance is low on the gingival side (cervical) and the optical transmittance increases toward the incisal side. For this reason, the dental bulk block of the present disclosure is economic because there is no need to separately characterize when manufacturing prosthesis unlike the existing method.

In addition, regarding the physical properties of natural teeth, the enamel, which is the surface layer of the teeth, has a high biaxial bending strength, and the dentin inside the enamel has relatively low strength, thereby playing a role in absorbing and dispersing external forces. In the present disclosure, a functionally graded material having gradations of physical properties, for example, especially biaxial flexural strength can be implemented due to depth-wise variation in microstructure through heat treatment, making it possible to reproduce very similar physical properties to the physical properties of natural teeth.

In the case of manufacturing a dental restoration using the dental bulk block of the present disclosure, machinability can be significantly improved. Specifically, for example, in one embodiment of the present disclosure, there is provided a method of manufacturing a dental restoration, the method including: manufacturing S30 a predetermined form of dental restoration by machining the above-described dental bulk block using a machining machine; and polishing or glazing S40 the dental restoration.

In the description above and below, the dental restorations include crowns, inlays, onlays, veneers, abutments, and the like.

Here, the glazing may be performed at a temperature in a range of 730° C. to 820° C. for a duration of 30 seconds to 10 minutes, and in this case, it may be a typical finishing heat treatment step that causes little change in optical transmittance. The glazing is usually performed within a temperature range in which the inherent optical transmittance of the bulk block does not change. During the glazing heat treatment, surface healing strength can be increased by more than 50%.

However, in a specific embodiment, in the method of manufacturing a dental restoration using the bulk block according to the present disclosure, the glazing may be used to adjust the optical transmittance of the machined dental restoration by performing a heat treatment of at least 825° C. That is, the glazing can be used for the purpose of adjusting the brightness by reducing the optical transmittance in the final finishing step after the machining the dental block into a dental restoration.

When a technician or user manufactures a dental restoration by machining a bulk block, there may be a case where the optical transmittance is unintentionally changed to a high level. In this case, if a conventional lithium disilicate-based bulk block is used, the block with the changed optical transmittance is discarded, and a new bulk block needs to be heat treated to have the desired optical transmittance through a predetermined heat treatment, and then the heat treated bulk block is machined again to obtain a dental restoration. However, in the case of using the bulk block according to the present disclosure, since the bulk block is a special bulk block having a fine crystalline phase, that is, the bulk block has the characteristic in which the optical transmittance thereof can be adjusted according to the heat treatment temperature, it is not necessary to re-machine a new bulk block. The optical transmittance of the dental bulk block machined into the dental restoration can be adjusted by the glazing process in a finishing stage in which the glazing is performed under predetermined conditions. Therefore, it is possible to simply shield colored teeth generated in the process of machining a bulk block into a dental restoration through glazing.

The glazing used for this purpose is preferably carried out at a temperature of at least 825° C. for a duration of 1 minute to 20 minutes.

Characteristically, in the case of the dental bulk block obtained according to the present disclosure, the cutting resistance against the tool during the machining can be significantly reduced when machining the bulk block using a machining machine. Specifically, as illustrated in FIGS. 1 and 2, the dental bulk block of the present disclosure may be a glass ceramic block including crystalline phases in an amorphous glass matrix, in which the crystalline phases include lithium disilicate as a main crystalline phase and lithium phosphate and at least one of cristobalite and tridymite as additional crystalline phases, and the dental bulk block is a functionally graded material (FGM) having gradations of size in the main crystalline phase along a depth direction thereof and having no interface at a gradation value change point at which a gradation value of size in the main crystalline phase changes. Such a dental bulk block having dimensions of 12 mm×14 mm×18 mm was cut at a speed of 250 RPM using a low-speed cutter (ISOMET low speed saw, Buehler, Germany) and a diamond electroplated wheel (2514485H17, Norton, USA), and the cutting time was measured. In the same way, for each of the most common (i.e., conventional) lithium disilicate block (Rosetta SM, manufactured by HASS Corp.), a zirconia reinforced lithium disilicate-based block (Celtra Duo, manufactured by DentsplySiron), and a lithium alumino silcate (LAS) reinforced lithium disilicate block (Nice, manufactured by Straumann), the cutting time was measured.

The cutting resistance (%) of each block was calculated on the basis of the measured cutting times. Specifically, the cutting time of the conventional lithium disilicate block was set as 100%, and the cutting time of each of the other blocks was converted into a percentage based on the cutting time of the conventional lithium disilicate block and calculated as the value of the cutting resistance.

The results are shown in FIG. 4.

The results of FIG. 4 shows that the conventional lithium disilicate block has the highest cutting resistance, the LAS crystallized glass and the zirconia reinforced crystallized glass have the second highest cutting resistance, and the block according to the present disclosure has the lowest cutting resistance. The results confirm that the glass ceramic block of the present disclosure is most machinable.

In a preferred embodiment, a glass composition containing 65.0% to 73.0% by weight of $SiO_2$, 12.0% to 14.0% by weight of $Li_2O$, 1.5% to 3.0% by weight of $Al_2O_3$, 0.12% to 0.22% by weight of ZnO, 2.8% to 3.5% by weight of $K_2O$, 0.3% to 1.0% by weight of $Na_2O$, and 2.0% to 6.0% by weight of $P_2O_5$ and satisfying an $Al_2O_3$ ($K_2O$+ZnO) molar ratio of 0.3 to 1.2 is weighted and mixed.

When $Al_2O_3$ is added to silicate glass, it enters the tetrahedral sites to act as a glass former, increases the viscosity, and reduces the mobility of ions. On the other hand, $K_2O$ and ZnO lower the viscosity and increase the ion mobility. As the ion mobility is increased, it is expected that cristobalite or tridymite grows in preferential orientation. Therefore, the $Al_2O_3$ ($K_2O$+ZnO) molar ratio is preferably in a range of 0.3 to 1.2 to facilitate the production of the present disclosure bulk block containing cristobalite or tridymite as an additional crystalline phase.

The glass composition may include $Li_2CO_3$ instead of $Li_2O$, and carbon dioxide ($CO_2$), which is a carbon component in $Li_2CO_3$, is released as a gas during the glass melting process. The glass composition may include $K_2CO_3$ and $Na_2CO_3$ instead of $K_2O$ and $Na_2O$, and carbon dioxide ($CO_2$), which is a carbon component in $K_2CO_3$ and $Na_2CO_3$, is released as a gas during the glass melting process.

The mixing uses a dry mixing process, and a ball milling process or the like can be used as the dry mixing process. The ball milling process will be described in detail. Starting materials are charged into a ball mill, and the ball mill is rotated at a constant speed to mechanically pulverize and uniformly mix the starting materials. The balls used in the ball mill may be balls made of a ceramic material such as zirconia or alumina, and the balls may have the same size or may have at least two different sizes. Depending on the target particle size, the sizes of the balls, the milling time, and the rotational speed per minute (rpm) of the ball mill are controlled. For example, to achieve the target particle size, the size of the balls may be selected in a range of about 1 mm to 30 mm, and the rotational speed of the ball mill may be set in a range of about 50 to 500 rpm. The ball milling is preferably performed for 1 to 48 hours depending on the target particle size. Through the ball milling, the starting materials are pulverized into fine particles having a uniform particle size, and the particles are uniformly mixed.

The mixed starting materials are placed in a melting furnace, and the melting furnace containing the starting materials is heated to melt the starting materials. Here, the term "melting" means that the starting materials are changed to a liquid state having a viscosity from a solid state. The melting furnace is preferably made of a material having a high melting point, high strength, and a low contact angle in order to inhibit the sticking of the melt. To this end, the melting furnace is preferably made of platinum (Pt), diamond-like-carbon (DLC), or chamotte or is preferably coated with platinum (Pt) or diamond-like-carbon (DLC).

The melting is preferably performed for 1 to 12 hours at 1,400 to 2,000° C. and atmospheric pressure. When the melting temperature is lower than 1,400° C., the starting materials may not be melted at all. When the melting temperature exceeds 2,000° C., it is not economical because excessive energy consumption is required. When the melting time is not sufficiently long, the starting materials may not be sufficiently melted. When the melting time is excessively long, it is not economical because excessive energy consumption is required. The temperature increase rate of the melting furnace is preferably about 5° C./min to 50° C./min. When the temperature increase rate of the melting furnace is excessively low, it takes a long time to melt the starting materials, resulting in reduction in productivity. When the temperature increase rate is excessively high, a large amount of the starting material volatilizes due to rapid temperature rise, resulting in poor physical properties of the produced crystallized glass. Therefore, it is preferable to raise the temperature of the melting furnace at a temperature increase rate within the above-mentioned range. The melting is preferably performed in an oxidizing atmosphere such as an oxygen ($O_2$) or air atmosphere.

The melt is poured into a predetermined mold to obtain a crystallized dental glass body having a desired shape and a desired size. The mold is preferably made of a material having a high melting point, high strength, and a low contact angle to inhibit the sticking of the glass melt. To this end, the mold is made of a material such as graphite and carbon. To prevent thermal shock, it is recommended to preheat the mold to 200° C. to 300° C. and pour the melt into the mold.

Since the melt contained in the mold is molded and cooled. After the cooling, the melt preferably undergoes an annealing step in which the molded body is slowly cooled at a predetermined decrease rate from 480° C. to 450° C. for a duration of 20 minutes to 2 hours.

Since the melt contained in the mold is molded and cooled, after the cooling process, the melt preferably undergoes an annealing step in which the melt is slowly cooled at a predetermined rate from 480° C. to 280° C. for a duration of 20 minutes to 2 hours. The annealing step reduces the stress variation in the molded product. Preferably, the annealing step completely removes the stress, which has a desirable effect on controlling the size of the crystalline phase and improving the homogeneity of the crystal distribution in the subsequent crystallization step. Therefore, the targeted functionally graded material can be obtained.

Here, the predetermined rate is preferably 1.6° C./minute to 10° C./minute.

The molded product having undergone the annealing process is transferred to a crystallization heat treatment sintering furnace for crystal nucleation and crystal growth. Through the crystal nucleation and crystal growth, a desired crystallized glass can be obtained.

FIG. 5 schematically shows a method of performing temperature-graded crystallization heat treatment according to the present disclosure. In the crystallization heat treatment of a block-type or ingot-type bulk block, the heat treatment is performed with a temperature gradient such that the upper end is heat treated at a relatively high temperature and the lower end is heat treated at a relatively low temperature.

In the above and below description, in the temperature-graded heat treatment step, devices and methods used are not specifically limited. For example, the heat treatment step may be performed in a temperature-graded furnace in an operating temperature range of 900° C. to 1,100° C. when taking the heat treatment temperature into account.

Through the temperature-graded heat treatment, the block has an ascending gradient of optical transmittance and a descending gradient of biaxial flexural strength from the part treated at a relatively high temperature to the part treated at a relatively low temperature. This is because the size of the crystals in the crystallized glass can be controlled with temperature. The crystalline phases generated after the temperature-graded heat treatment include lithium disilicate, and additional crystal phases including lithium phosphate and at least one of cristobalite and tridymite, and the main crystalline phase has a grain size gradient in which an average grain size is 0.05 μm to 1.5 μm when the heat treatment is performed with a temperature gradient of 760° C. to 880° C.

On the other hand, for the bulk block obtained according to the present disclosure, the grain size variation of the crystalline phase in the depth direction was analyzed, and the results are shown in FIG. 6.

In addition, for the bulk block obtained according to the present disclosure, the biaxial flexural strength variation in the depth direction was measured, and the results are shown in FIG. 6.

While the present disclosure has been described with reference to exemplary embodiments, those skilled in the art will appreciate that the exemplary embodiments are presented only for illustrative purposes and the present disclosure is not limited to the disclosed exemplary embodiments. On the contrary, it will be understood that various modifications and equivalents thereto are possible.

The present disclosure relates to a dental bulk block for cutting machining, which is useful for the manufacture of artificial teeth with similar structural characteristics to natural teeth, and a method for manufacturing the same.

The dental bulk block according to the present disclosure is used to manufacture artificial dental restorations having multi-gradation optical transmittance or physical properties like natural teeth with high reproducibility through only cutting machining such as CAD/CAM without using additional processes. The dental bulk block can shorten the time and process of manufacturing artificial tooth prostheses, and can increase the structural stability in terms of force distribution by functionally grading the physical properties. Such a dental bulk block can be manufactured by applying a simple graded-temperature heat treatment process to a predetermined single glass composition.

The invention claimed is:

1. A dental bulk block for cutting machining, the dental bulk block being a glass ceramic block comprising crystalline phases in an amorphous glass matrix, the crystalline phases comprising lithium disilicate as a main crystalline phase and lithium phosphate and at least one of cristobalite and tridymite as additional crystalline phases, wherein the dental bulk block is a functionally graded material (FGM) having gradations of size in the main crystalline phase along a depth direction thereof and having no interface at a gradation value change point at which a gradation value of size in the main crystalline phase changes, and wherein the glass matrix comprises 65.0% to 73.0% by weight of $SiO_2$, 12.0% to 14.0% by weight of $Li_2O$, 1.5% to 3.0% by weight of $Al_2O_3$, 0.12% to 0.22% by weight of ZnO, and 2.8% to 3.5% by weight of $K_2O$, 0.3% to 1.0% by weight of $Na_2O$, and 2.0% to 6.0% by weight of $P_2O_5$, and satisfies an $Al_2O_3/(K_2O+ZnO)$ molar ratio of 0.3 to 1.2.

2. The dental bulk block of claim 1, wherein the gradations of size in the main crystalline phase are formed such that an average grain size falls within a range of 0.05 μm to 1.5 μm.

3. The dental bulk block of claim 1, wherein the dental bulk block has gradations of optical transmittance in the depth direction.

4. The dental bulk block of claim 3, wherein the gradations of optical transmittance are within a range of 25% to 40% based on a wavelength of 550 nm.

5. The dental bulk block of claim 3, wherein the gradations of optical transmittance appear within a depth range of 0.5 mm or less in the depth direction.

6. The dental bulk block of claim 5, wherein the gradations of optical transmittance appear even in a depth range of 0.31 mm in the depth direction.

7. The dental bulk block of claim 1, wherein the dental bulk block has gradiations of L*, a*, and b* values measured through chromacity analysis in the depth direct4ion, and a color deviation (ΔE) value changes even within a depth range of 0.31 mm in the depth direction.

8. The dental bulk block of claim 1, wherein the dental bulk block has a crystallinity of 40% to 70%.

9. The dental bulk block of claim 1, wherein the dental bulk block has gradations of biaxial flexural strength in the depth direction.

10. The dental bulk block of claim 9, wherein the gradations of biaxial flexural strength are within a range of 180 MPa to 420 MPa.

11. The dental bulk block of claim 1, wherein the dental bulk block is made of a continuous glass matrix.

12. A method for manufacturing a dental bulk block according to claim 1 for cutting machining, the method comprising: producing a predetermined form of block by melting a glass composition containing 65.0% to 73.0% by weight of $SiO_2$, 12.0% to 14.0% by weight of $Li_2O$, 1.5% to 3.0% by weight of $Al_2O_3$, 0.12% to 0.22% by weight of ZnO, 2.8% to 3.5% by weight of $K_2O$, 0.3% to 1.0% by weight of $Na_2O$, and 2.0% to 6.0% by weight of $P_2O_5$ and satisfying an $Al_2O_3/(K_2O+ZnO)$ molar ratio of 0.3 to 1.2, shaping and cooling the molten glass composition in a mold, and annealing the resulting block while changing a temperature from 480° C. to 280° C. at a predetermined rate for a duration of 20 minutes to 2 hours; and heat treating the block t a temperature in a range of 760° C. to 880° C. while giving a temperature gradient along the depth direction of the block.

13. The method of claim 12, wherein the heating treating is performed such that an upper layer of the block is heat treated in a temperature range of 840° C. to 880° C. and a lower layer of the block is heat treated in a temperature range of 760° C. to 800° C.

14. The method of claim 12, wherein the heat treating is performed in a temperature-graded furnace in an operating temperature range of 900° C. to 1100° C. for a duration of 1 minute to 40 minutes.

15. A method for manufacturing a dental restoration, the method comprising: manufacturing a predetermined form of dental restoration by machining the dental bulk block of claim 1 using a machining machine; and polishing or glazing the dental restoration.

16. The method of claim 15, wherein the glazing is performed in a temperature range of 730° C. to 820° C. for a duration of 30 seconds to 10 minutes.

17. The method of claim 15, wherein the glazing is performed to adjust the optical transmittance of the machined dental restoration through heat treatment at 825° C.

18. The method of claim 17, wherein the glazing is performed at a temperature of at least 825° C. for a duration of 1 minute to 20 minutes.

* * * * *